(12) United States Patent
Mauk et al.

(10) Patent No.: US 11,986,820 B2
(45) Date of Patent: *May 21, 2024

(54) POINT-OF-CARE DIAGNOSTIC METHODS USING CAPILLARY-ACTION MICROFLUIDIC DEVICES

(71) Applicants: Michael G. Mauk, Philadelphia, PA (US); Dharma Teja Varapula, Philadelphia, PA (US); Sirisha Phanithra Gutta, Pittsburgh, PA (US)

(72) Inventors: Michael G. Mauk, Philadelphia, PA (US); Dharma Teja Varapula, Philadelphia, PA (US); Sirisha Phanithra Gutta, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/820,622

(22) Filed: Mar. 16, 2020

(65) Prior Publication Data
US 2021/0039094 A1    Feb. 11, 2021

Related U.S. Application Data

(63) Continuation of application No. 15/489,684, filed on Apr. 17, 2017, now Pat. No. 10,596,566.
(Continued)

(51) Int. Cl.
*C12Q 1/68* (2018.01)
*B01L 3/00* (2006.01)
(Continued)

(52) U.S. Cl.
CPC ....... *B01L 3/502715* (2013.01); *B01L 3/5023* (2013.01); *B01L 3/50273* (2013.01); *B01L 7/52* (2013.01); *B01L 7/525* (2013.01); *B01L 2200/0621* (2013.01); *B01L 2200/10* (2013.01); *B01L 2300/0654* (2013.01); *B01L 2300/0825* (2013.01); *B01L 2300/126* (2013.01); *B01L 2400/0406* (2013.01); *B01L 2400/0457* (2013.01); *C12Q 1/6844* (2013.01)

(58) Field of Classification Search
CPC .................................................... C12Q 1/6844
See application file for complete search history.

(56) References Cited

U.S. PATENT DOCUMENTS

| | | | |
|---|---|---|---|
| 8,821,810 B2 * | 9/2014 | Whitesides | ....... B01L 3/502738 435/288.5 |
| 2009/0226892 A1 * | 9/2009 | Mori | ....................... C12P 19/34 435/6.12 |

(Continued)

*Primary Examiner* — Kenneth R Horlick
(74) *Attorney, Agent, or Firm* — Calderone McKay LLC

(57) ABSTRACT

Methods that integrates processing and an analysis of a sample are disclosed and include use of a testing device that integrates nucleic acid isolation, isothermal amplification and detection wherein a sample and reagents are transported through a capture/binding membrane by capillary forces and the positioning of a slidebar that supports said binding membrane. In the practice of the methods, flow control and fluid actuation are effected by the position of a slidebar of the device which makes a fluidic connection through the capture membrane situated between a reservoir of liquid on the device and an absorbing pad, and where a sequence of operations for sample loading, washing, optionally amplification, and optical detection of analytes can be done conveniently and rapidly at the point of care.

18 Claims, 9 Drawing Sheets

Specification includes a Sequence Listing.

Related U.S. Application Data

(60) Provisional application No. 62/323,253, filed on Apr. 15, 2016.

(51) Int. Cl.
*B01L 7/00* (2006.01)
*C12Q 1/6844* (2018.01)

(56) References Cited

U.S. PATENT DOCUMENTS

| | | | | |
|---|---|---|---|---|
| 2011/0117540 | A1* | 5/2011 | Cary | G01N 33/558 |
| | | | | 435/5 |
| 2011/0294205 | A1* | 12/2011 | Hukari | G01N 1/405 |
| | | | | 435/325 |
| 2013/0309679 | A1* | 11/2013 | Ismagilov | B01L 3/5027 |
| | | | | 435/6.12 |
| 2015/0376692 | A1* | 12/2015 | Esfandyarpour | G01N 27/745 |
| | | | | 506/38 |

* cited by examiner

MG Mauk "Capillary Action Microfluidic Device for Point-of-Care Diagnostics"

Top View

SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide Forward Primer F3

<400> SEQUENCE: 1
gatctgaatc cgaccaaccg                                        20

<210> SEQ ID NO 2
<211> LENGTH: 18

```
<212> TYPE: DNA
<213> ORGANISM: Artificial Sequence
<220> FEATURE:
<223> OTHER INFORMATION: synthetic oligonucleotide Reverse Primer B3

<400> SEQUENCE: 2
aacgcccacg ctctcgca                                                         18

<210> SEQ ID NO 3
<211> LENGTH: 41
<212> TYPE: DNA
<213> ORGANISM: Artificial Sequence
<220> FEATURE:
<223> OTHER INFORMATION: synthetic oligonucleotide FIP Primer

<400> SEQUENCE: 3
aaatccgtcc agtggttttt ttgaaaatcg ttgtatctcc g                               41

<210> SEQ ID NO 4
<211> LENGTH: 46
<212> TYPE: DNA
<213> ORGANISM: Artificial Sequence
<220> FEATURE:
<223> OTHER INFORMATION: synthetic oligonucleotide BIP Primer

<400> SEQUENCE: 4
ccgaaaccac tggacggatt tttattttta atctaaaaca aacatc                         46

<210> SEQ ID NO 5
<211> LENGTH: 41
<212> TYPE: DNA
<213> ORGANISM: Artificial Sequence
<220> FEATURE:
<223> OTHER INFORMATION: synthetic oligpnucleotide FIP Primer

<400> SEQUENCE: 5
aaatccgtcc agtggttttt ttgaaaatcg ttgtatctcc g                               41

<210> SEQ ID NO 6
<211> LENGTH: 46
<212> TYPE: DNA
<213> ORGANISM: Artificial Sequence
<220> FEATURE:
<223> OTHER INFORMATION: synthetic oligonucleotide BIP Primer

<400> SEQUENCE: 6
ccgaaaccac tggacggatt tttattttta atctaaaaca aacatc                         46
```

POINT-OF-CARE DIAGNOSTIC METHODS USING CAPILLARY-ACTION MICROFLUIDIC DEVICES

CROSS REFERENCE TO RELATED APPLICATIONS

This application is a continuation of co-pending U.S. patent application Ser. No. 15/489,684, filed Apr. 17, 2017, entitled, "Capillary-Action Microfluidic Device for Point-of-Care Diagnostics", which claims the benefit under 35 U.S.C. § 119(e) of U.S. Provisional Application Ser. No. 62/323,253 filed Apr. 15, 2016, entitled, "Capillary-Action Microfluidic Chip for POC Diagnostics," the entire disclosures of each of which are incorporated herein by reference.

BACKGROUND ART

The present invention relates to devices and methods of chemical or biochemical tests that are portable, fast, and easy to use, and in particular, but not exclusively, to tests that can be performed outside of laboratories, and by non-technically-trained operators. More particularly, this invention can be used for in vitro medical diagnostics tests wherein clinical specimens such as blood, saliva, urine, stool, and similar, or other samples such as derived from food, plants, animals, and insects, can be tested at the point-of-care, such as a doctor's or dentist's office, pharmacy, school infirmary, border control, or rural clinic, or in the field such as a farm, food processing plant, restaurant kitchen, or zoo. Other applications include environmental monitoring for microorganisms or detection of bioterrorism agents.

This invention is particularly suited for tests that require sample processing to better enable the detection of analytes. For example, many disease conditions, as well as contamination with infectious agents, are signaled by specific biomarkers specific to the pathogen (e.g., viral or bacterial genes) or the host response to the pathogen (e.g., antibodies against infectious agents). Such biomarkers include proteins, nucleic acids (RNA and DNA), toxins, and metabolites. Methods of detecting such biomarkers include immunoassays for proteins and other large molecules, enzymatic nucleic acid amplification such as polymerase chain reaction (PCR), and a host of other methods that rely on highly-specific binding between proteins and other proteins or biomolecules, or nucleic acid hybridization, in combination with reporters such as dyes and nanoparticles, in optical or electrochemical systems. There has been much technical progress in the miniaturization of detection methods. For instance, polymerase chain reactions for amplification of target nucleic acid sequences can be implemented in small chips. However, direct amplification of crude or raw samples such as blood, saliva, urine, food, drinking water, and environmental samples can severely compromise the viability of such tests, with regard to reproducibility, sensitivity, and specificity. Alternatively, amplification tests work better for samples that are processed prior to amplification. For example, plasma or serum is first separated from whole blood, microorganisms and viruses in the plasma are then lysed to release their nucleic acids in soluble form, the nucleic acids are then isolated in purified, concentrated form for enzymatic amplification. This processing removes substances in the sample that are known to inhibit enzymatic amplification. Also, such processing provides for more consistent amplification, reducing variations due to sample variability. Third, it is important to concentrate nucleic acids that may be sparse in the raw sample. Nucleic acids that have a low concentration in the sample require a relatively large sample volume. On the other hand, most enzymatic amplifications used reaction volumes of 10 to 100 microliters. This comparatively small reaction volume facilitates temperature control and economizes enzymes, with sample volumes of 10 to 30 microliters being common. A concentrated amplification reaction also provides more optical contrast (difference between optical properties of reaction mixture and surrounding background) for optical methods of detection such as fluorescence, luminescence, optical absorption, and also electrochemical methods for detecting the amplification product. However, sample sizes limited to this range, i.e., wherein the unconcentrated sample is added as a component of the total reaction volume, will not contain sufficient amounts of target for reliable amplification and detection. A specific example of considerable medical interest relates to viral load measurements, such as commonly used as a diagnostic for monitoring the progression and treatment of HIV-infected subjects. Viral loads in the range of 1 to 1000 viruses per milliliter of blood need to be measured, thus indicating sample sizes on the range of 100 to 1000 microliters. Ultimately, for the reasons discussed above, the enzymatic reactions for detecting HIV virus be designed for reaction volumes of 10 to 1000 microliters. Accordingly, one object of this invention is a means to concentrate the nucleic acid from samples into a much smaller volume for amplification. As a typical example, the total nucleic acid extracted from 500 microliters of blood can be concentrated in relatively purified form to a volume of 10 microliters (sometimes called an elution in solid-phase extraction methods in general and in nucleic acid purification methods in particular), or can be immobilized on a solid phase such as a porous or fibrous membrane of several to tens of cubic millimeters in volume. Currently, this is done in laboratories with spin columns and centrifuges, but this method is not readily amenable to simple diagnostics devices for use at the point of care.

There is considerable interest in diagnostic devices that integrate all sample processing steps with enzymatic amplification and detection. An objective is to reduce burdening the operator of the test with tasks such as sample processing, preparation of reagents, addition of reagents to the device, sample transfer between steps, and the like, in order to make the test more convenient, reliable, and appropriate for a wider range of applications, especially for use in resource-limited settings. Another desirable feature for POC diagnostics is to avoid or minimize the need for supporting instrumentation such as pumps, temperature controllers, actuators, and similar devices. An autonomous device, that can work independently of an auxiliary equipment would broaden the venues of application of such devices, including home use by consumers.

There has been considerable work over the last twenty years on developing miniaturized fluidic systems ('microfluidics') that can process and analyze samples. A useful categorization of microfluidics devices is based on their structure and mode of operation. Many devices are based on plastic structures ('chip') in which a network of channels, chambers, manifolds, filters, inlet and outlet ports, and other components are formed. Such devices can perform relatively sophisticated processing and analysis of samples, essentially mimicking the types of operations done on the lab bench. However, these types of devices require means for flow control and fluid actuation. They typically incorporate some types of valves or other flow control devices, and. pumping mechanisms for moving fluids through the microfluidic network. Alternatively, these functions can be provided by external instrumentation such as programmable syringe pumps. Such devices tend to be relatively complicated to fabricate and operate, making them inappropriate for many point of care applications.

A second type of device is based on moving fluids by the wicking action of porous materials. The lateral flow strip used in the home pregnancy test is a well-known example. A few drops of sample (e.g., urine or blood) are blotted on one end of a nitrocellulose paper strip, and capillary action moves the sample through zones where various substances or reagents (e.g., antibodies or antigens) are immobilized and can interact with analytes in the sample to produce a detectable signal. In the last decade, there has been much work on generalizing this approach, so-called 'paper microfluidics' to realize more complicated assays. In some versions of paper-based microfluidics, channels and flow paths defined by wax printing on filter paper. There are two limitations with paper microfluidics. Firstly, the flow control, especially for processes that require a sequence of fluid operations, is difficult to realize, as paper microfluidic devices do not feature conventional valves or flow-gating devices, such that flow streams can be directed along certain pathways, or flow can be turned on or off. Different flow control features, often of a mechanical nature or mechanism, could be incorporated into such paper-based microfluidic devices to give them more functionality. Such features would add complexity with respect to fabrication and operation, as well as reduced reliability.

A second limitation of paper-based microfluidic devices described in the art is that the volumes of sample and other reagents are comparatively small, often in the 1 to 10 microliter range. This aspect can be distinguished from nlike plastic chips with channels and reservoirs that can be microfluidic formats scale to large sample volumes. Large volumes will overwhelm the wicking capacity of areas of the paper designated for flow paths. Second, liquid reagents and buffers are not self-contained on the device, or have to he actuated from pouches and other compartments, or added (e.g., by pipetting) at the time of use by the operator.

In summary, it is difficult to simultaneously gain the advantages of plastic chips (e.g., compatibility with large liquid volumes and more sophisticated flow control), and paper microfluidics (e.g., passive fluid actuation, i.e., no active pumping) without incurring limitations inherent in either approach. Two recent examples illustrate this dilemma. Whitesides et al. (U.S. Pat. No. 8,821,810, Sep. 2, 2014) describes a slider chip where a moving member provides or modifies a changeable flow path to implement a sequence of fluid operations. However, Whitesides et al. does not provide for a means automatically utilize fluid volumes stored on the chip itself, and describe pipetting steps to add liquid buffer solutions to the chip. Imagilov et al, (US Patent Application Publication US 2013/0309679 A1, Nov. 21, 2013) show a microfluidic device with a sliding component that provides a sequenced operation of fluid transfer steps. However, fluid flow is effected by application of pressure at the inlet of the microfluidic network. In either case, operator intervention and/or connection of the device to supporting devices is then required. For simple diagnostics applications, this falls short of complete automation of "sample in, report out," without relying on external instrumentation, addition of reagents, dislodging liquids from pouches, or other 'hands on' control.

The present invention combines a slider mechanism and wicking action with absorption pads. The slider supports a porous membrane which acts as a binding phase in solid-phase extraction. The slide action provides a temporary fluid connection between a sample well, or a reservoir of liquid prestored on the chip, and an absorbing pad. This structure can be repeated as often as needed to implement more complicated assays. In distinction to prior disclosed approaches, the present invention can be scaled for the large sample and reagent volumes needed for sensitive assays, does not require the addition of liquids after sample introduction, and needs only occasional pushing of a slider, for which timing is not crucial. Also, the approach enables a significant concentration (e.g., from 10 to 1000 times) of the analyte of interest, so that in the detection step, the analyte has been concentrated from a large sample into a much smaller volume.

SUMMARY OF THE EMBODIMENTS

We describe a point-of-care ((POC) diagnostics device integrating solid-phase nucleic acid extraction and isolation, isothermal enzymatic amplification, and real-time fluorescence detection that uses only wicking action for fluidactuation. Liquids are transported between processing stages by the wicking action of absorption pads, such that flow is controlled by a simple movement of a sliding part, obviating the need for pumps, valves or manual pipetting. The device features a slider-mounted fibrous or otherwise porous media, sometimes called a 'membrane' or binding phase art, that functions as capture media to adsorb components, such as nucleic acids, from a liquid phase that flows through the membrane. By moving the slider, the membrane makes successive fluidic connections between a series of reservoirs containing sample, wash(es) and elution buffer, and absorption pads which draw liquids of various compositions through the membrane, the effect of which is to isolate, purify, and concentrate the analyte. The captured analyte is eluted from the membrane into a reaction site, or otherwise placed in fluidic contact with a liquid reaction mixture. Said reaction can be an enzymatic amplification process to increase the amount of analyte, facilitating its detection by fluorescence, optical absorption, luminescence, light scattering, or electrochemical means. A constant-temperature enzymatic amplification method serves as a particularly convenient means to amplify the target. Loop-mediated AMPlification (LAMP) reagents, incubated by heating to 65° C., and monitoring a fluorescent signal with a CCD camera, e.g,, such as with a smartphone. Another variation is to use an enzymatic amplification technique that generates a luminescent signal with production of amplicon as described in O. A. Gandelman et al. (2010, "Novel bioluminescent quantitative detection of nucleic acid amplification in real-time" *PLoS ONE* 5(11) e14155). This avoids limitations associated with autofluorescence or background fluorescence that reduce sensitivity of the detection. Another feature is to dry all of the enzymatic amplification reagents (including polymerases, oligos primers, dyes, reporter reagents, salts, dNTPs, etc. . . . ) in desired proportion on the porous membrane or wicking pads. Thus, the infiltration of liquid by wicking action will reconstitute the enzymatic reaction in correct proporations to amplify the nucleic acid contained in the liquid. This simple plastic device with one moving part implements a common protocol for molecular diagnostics eliminating the need for sample reagent handling between steps. Results for detecting *Salmonella* bacteria nucleic acid are reported.

DETAILED DESCRIPTION OF THE EMBODIMENTS

Figure 1:
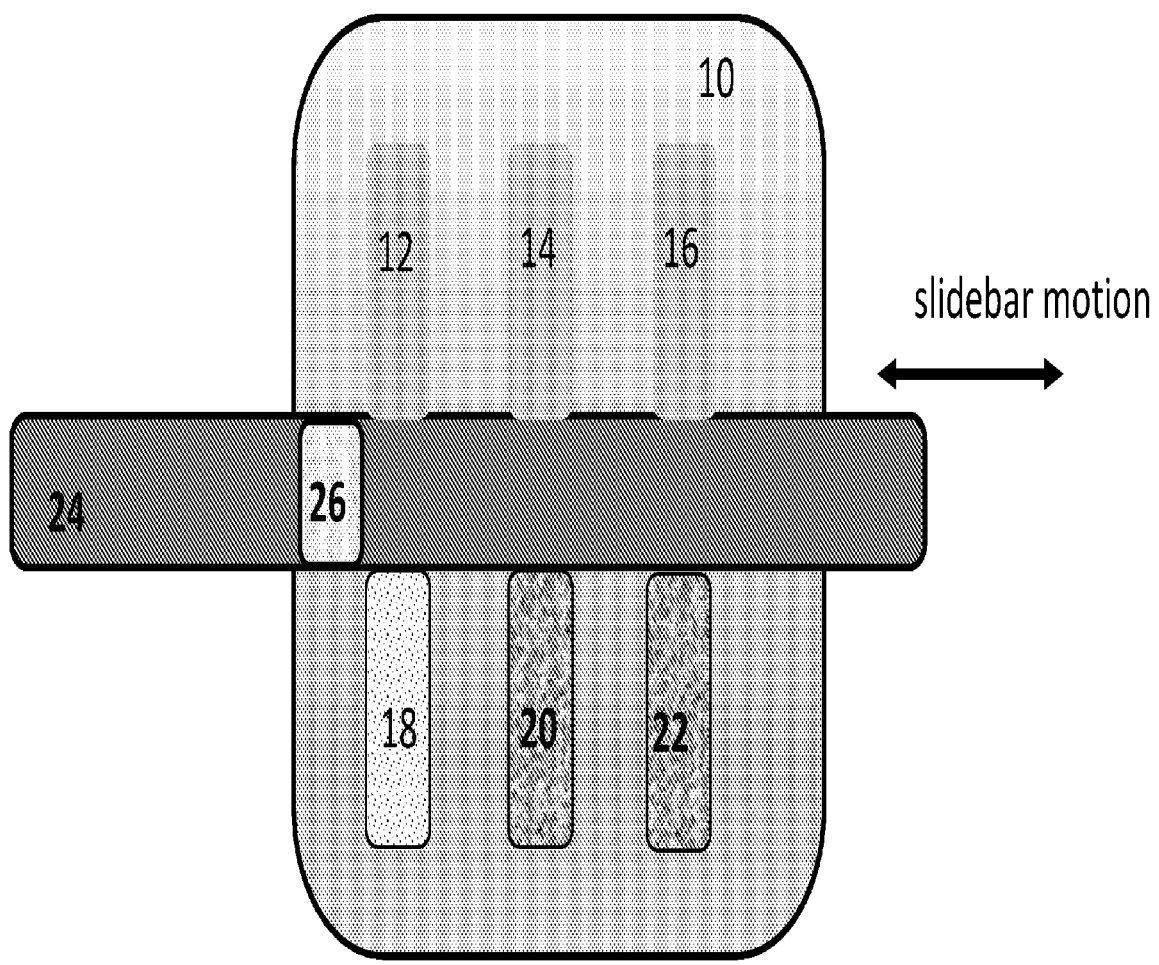
FIG. 1 shows the most basic components of the device.

Integrated Capillary-Driven Sample Processing for Point-of-Care Microfluidics-Based Molecular Diagnostics
Introduction Molecular diagnostics, i.e., nucleic acid amplification tests (NAATs), provide the most sensitive and specific means for detection of pathogen-associated biomarkers. In contrast to immunoassays and cell-based methods, NAATs derive their superior sensitivity from sequence-specific enzymatic amplification of a DNA or RNA analyte, typically providing a million-fold increase of the target NA sequence and thus facilitating detection and quantification by optical or electrochemical sensors. Novel, low-cost formats for portable point-of-care molecular diagnostics are enabled by miniaturization in general, and more particularly, 'lab-on-a-chip' microfluidic-based sample processing. Other useful technologies include isothermal nucleic acid amplification (as opposed to polymerase chain reaction which requires precise temperature cycling), lyophilization (freeze drying) of enzymes for pre-loading and long-term (on-chip) storage of reagents; inexpensive electronics, microcontrollers, and sensors; rapid prototyping (e.g., 3D printing and laser machining), and low-cost, high-volume manufacturing of plastic parts (e.g., injection molding and stamping or embossing).

Further, there is a recent trend in leveraging POC diagnostics devices with smartphones for computation, control, communication, data logging, and especially, using smartphone CCD cameras for fluorescence monitoring in real-time NA amplification. Diagnostics tests previously restricted to well-equipped medical laboratories staffed by skilled and trained technicians, requiring turn-around times of 24-48 hours, and costing the consumer on the order of $100 per test, can now be performed outside of laboratories by layman in a time frame of 10 to 60 minutes and at a per test cost of around $10. POC testing in doctors' and dentists' offices, pharmacies, school infirmaries, and border crossings, and for home use will support new paradigms for delivery of medical care and assuring public health, especially in the developing world. Related applications for such portable, rapid assays include testing for food or water microbial contamination, monitoring disease in animals and plants, and detection of biowarfare agents.

While direct amplification of DNA or RNA in a raw sample, such as whole blood, plasma, serum, urine, or oral fluid is feasible, it is generally preferable to include sample processing to extract, purify and concentrate the nucleic acid prior to amplification. This nucleic acid isolation step removes inhibitor substances from the sample that interfere with the enzymatic amplification, and thus allows greater sensitivity, specificity, reliability, and more consistent results. Further, the concentration of target NA contained in a 100 to 1000 μl sample volume to a smaller amplification reaction volume (~10 μl) reduces the amount of enzymes required, facilitates closer temperature regulation, and provides better signal contrast for optical or electrochemical detection. The integration of sample preparation (lysis, isolation, and concentration) with amplification and detection is thus an important aim of microfluidics-based molecular diagnostics for point-of-care diagnostics.

Solid-phase extraction of nucleic acids from lysates is the most a common method for nucleic acid isolation, and is amenable to microfluidic formats. In benchtop protocols, a spin column is used, wherein the crude sample is mixed with a lysis/binding agent that disrupts cells and viruses and solubilizes nucleic acids. The lysate is then filtered through a porous nucleic acid binding media, such as a silica glass fiber or cellulose membrane. The binding agent promotes adsorption of nucleic acids to the solid phase, separating the remaining lysate components as flow through. In a second step, residual proteins and other cell or sample debris are washed from the membrane by ethanol-water solutions. The nucleic acid is then eluted (in a volume 10 to 100 times smaller than the original sample) in pure form, suitable for enzymatic amplification, such as PCR (polymerase chain reaction), or more recently-developed isothermal amplification techniques such as LAMP (loop-mediated amplification), RPA (rapid polymerase amplification), and HDA (helix-dependent amplification). An intercalating DNA binding dye allows real-time fluorescence monitoring of the amplification, simplifying the device the need for end-point detection of the amplicon, and permitting quantification of the target NA if needed. Alternatively, the amplification can be coupled to bioluminescent or chemiluminescence reactions that eliminate the need for an external light source and filters, and avoid interference from non-specific 'background' autofluorescence.

A general theme of POC diagnostics development is to reduce or eliminate sample and reagent handling steps in order to provide testing that can be done with minimal operator intervention, while still maintaining low cost and simplicity. The US Food and Drug Administration guidelines for approval of POC diagnostics demand minimal sample handling, and no pipetting or centrifugation steps. Currently, lateral flow strip immunoassays, such as used in home pregnancy and drugs-of-abuse tests, meet this criteria, and represent a prominent standard for simplicity, ease-of-use, and cost. Lateral flow strip immunoassays are a highly developed and elegant where capillary forces and wicking action of absorption pads allows a simplified operation involving merely addition of raw sample, followed by readout of results. Such instrumentation-free testing proves challenging for molecular diagnostics due to the required multi-stage sample processing, transfer of sample between stages, addition of reagents or buffers, and temperature control Nevertheless, there has been an upsurge of interest in more complicated processing using 'paper' microfluidics that use capillary forces and wicking action in porous materials for sample processing [refs].

Here, we describe a device that integrates nucleic acid isolation, isothermal amplification and detection where the sample and reagents are transported through a NA-binding membrane by capillary forces. The sample processing steps are actuated by simply moving a slider bar on which the membrane is mounted; no pipetting or addition of reagents is needed. As the slider is translated, sample, washes, and elution buffers are successively wicked through the membrane. The slider translation is discrete, and can be controlled by stops. Relatively large volumes (~100 μl) of liquid can be actuated. This may be contrasted to so-called paper microfluidics and lateral flow strips where the flow paths are porous layers and sample and reagent volumes are typically in the 1-10 μl range. The isolated nucleic acid is then detected by real-time isothermal amplification. This approach offers a molecular diagnostics device that implements that processing steps of commonly-used benchtop protocols but that is practically as easy to use as ubiquitous lateral flow strip immunoassays. This approach combines the features of conventional microfluidics 'chips' made in hard plastics (acrylic, polycarbonate) or soft polymers (PDMS) with networks of conduits, channels, chambers, and manifolds for storing and manipulating a wide variety of liquids (clinical specimens, buffer or salt solutions, water, alcohols) in volumes ranging from microliters to milliliters, with the advantages of "passive" paper- or capillary-based devices that circumvent the need for external pumping and valving or other flow control mechanisms.

Design Concepts and Issues

Figure 2A:
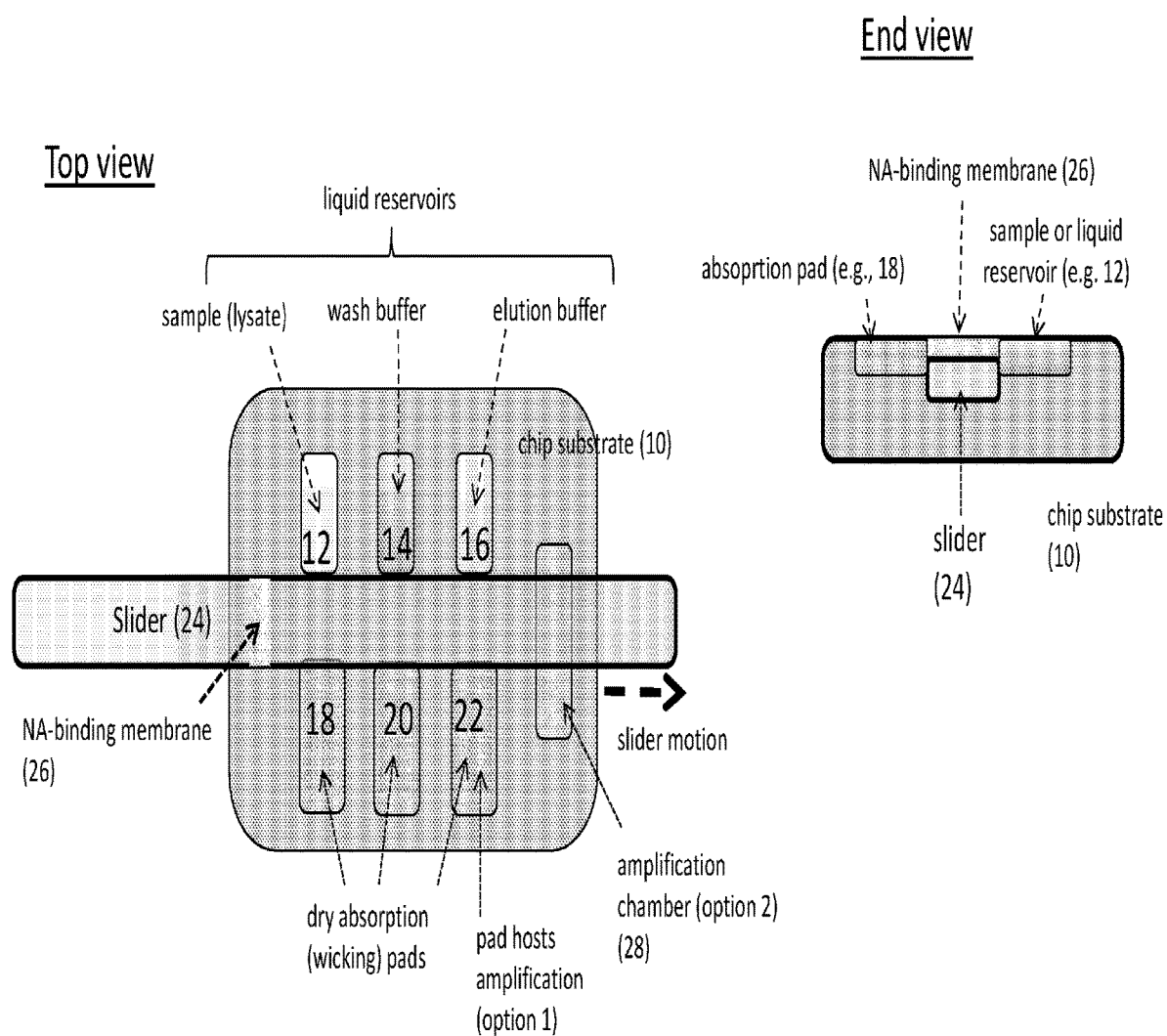
FIGS. 2a, 2b, 2c, 2d and 2e show the device in successive stages of operation, processing and analyzing a sample.
Figure 2B:
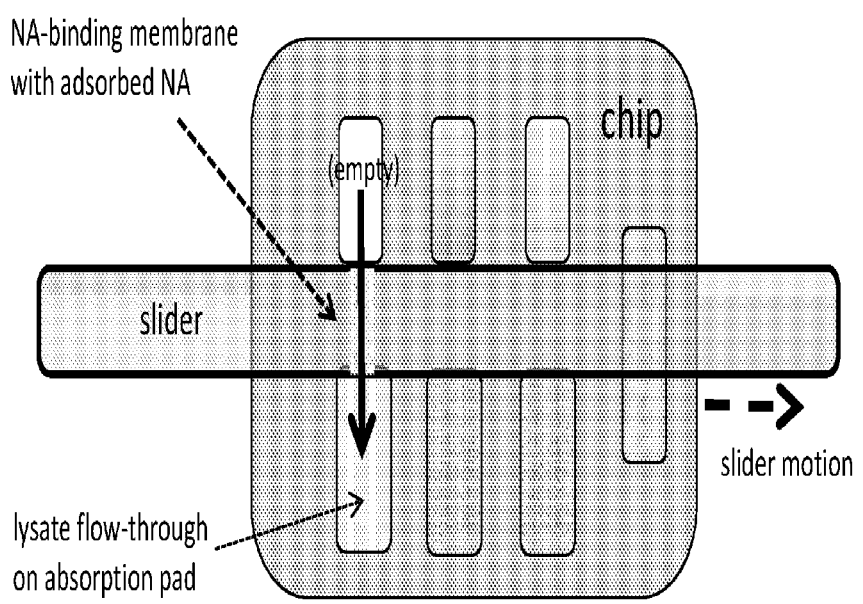
Figure 2C:
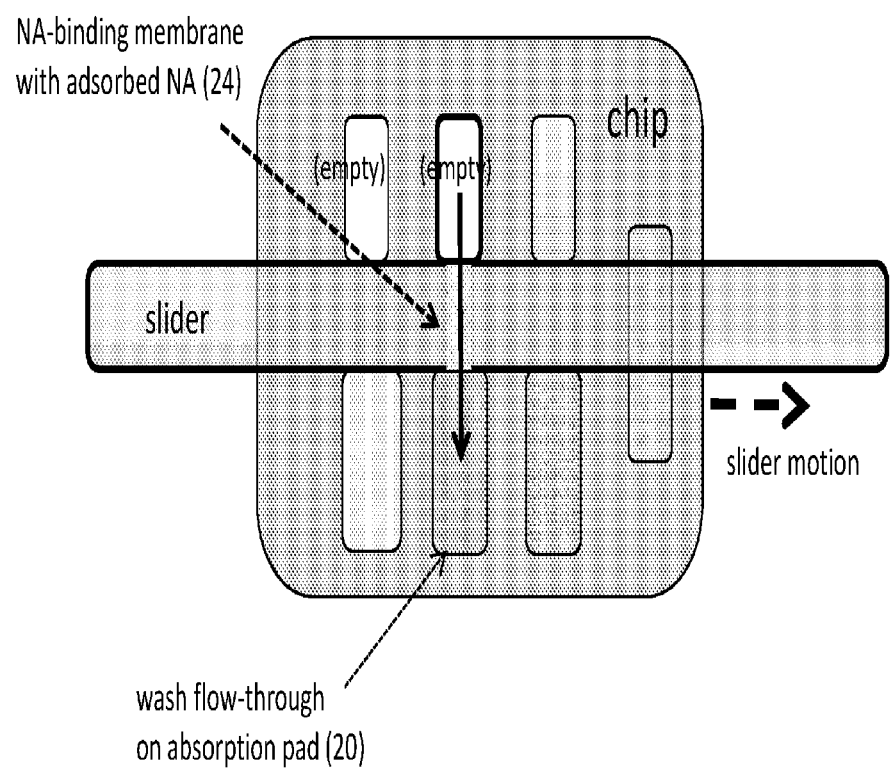
Figure 2D:
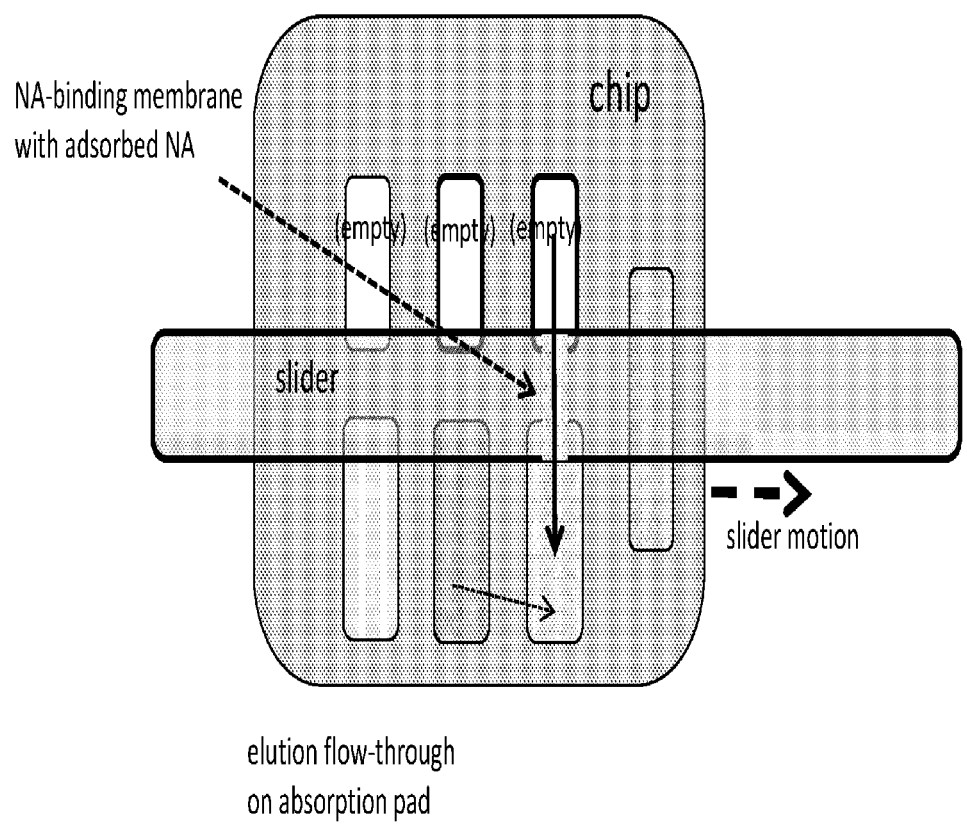
Figure 2E:
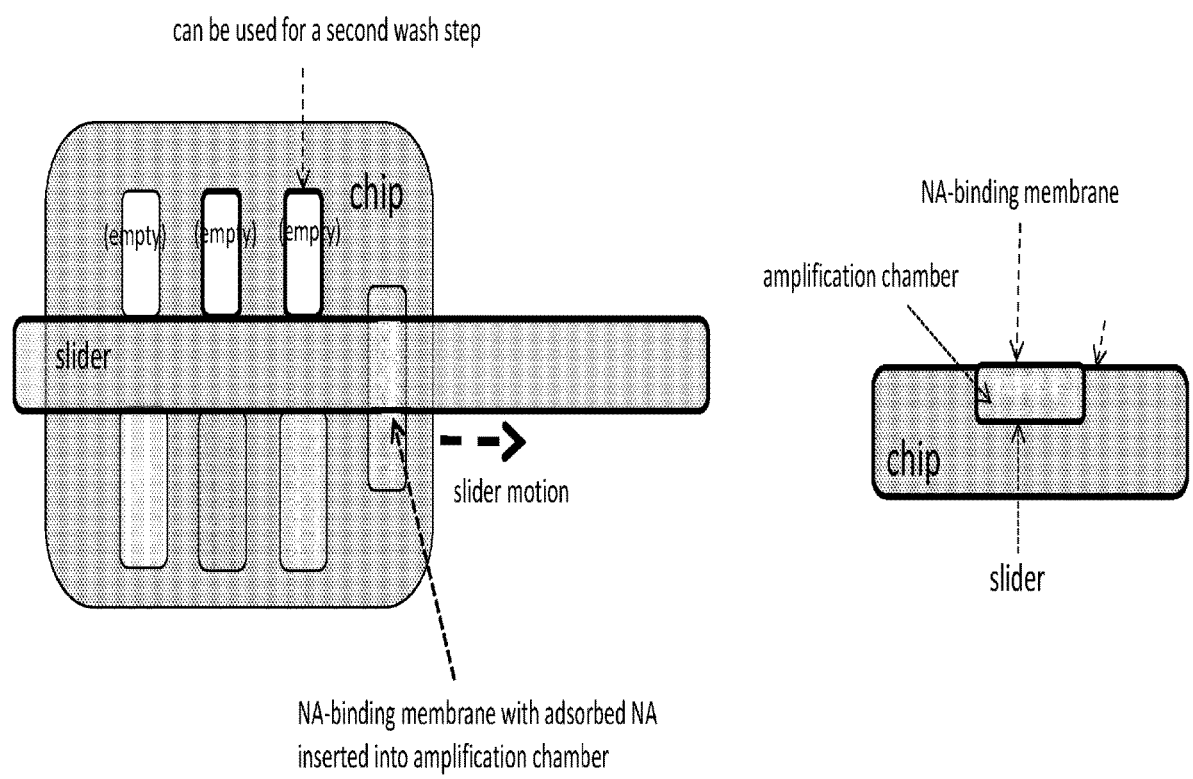
Figure 3:
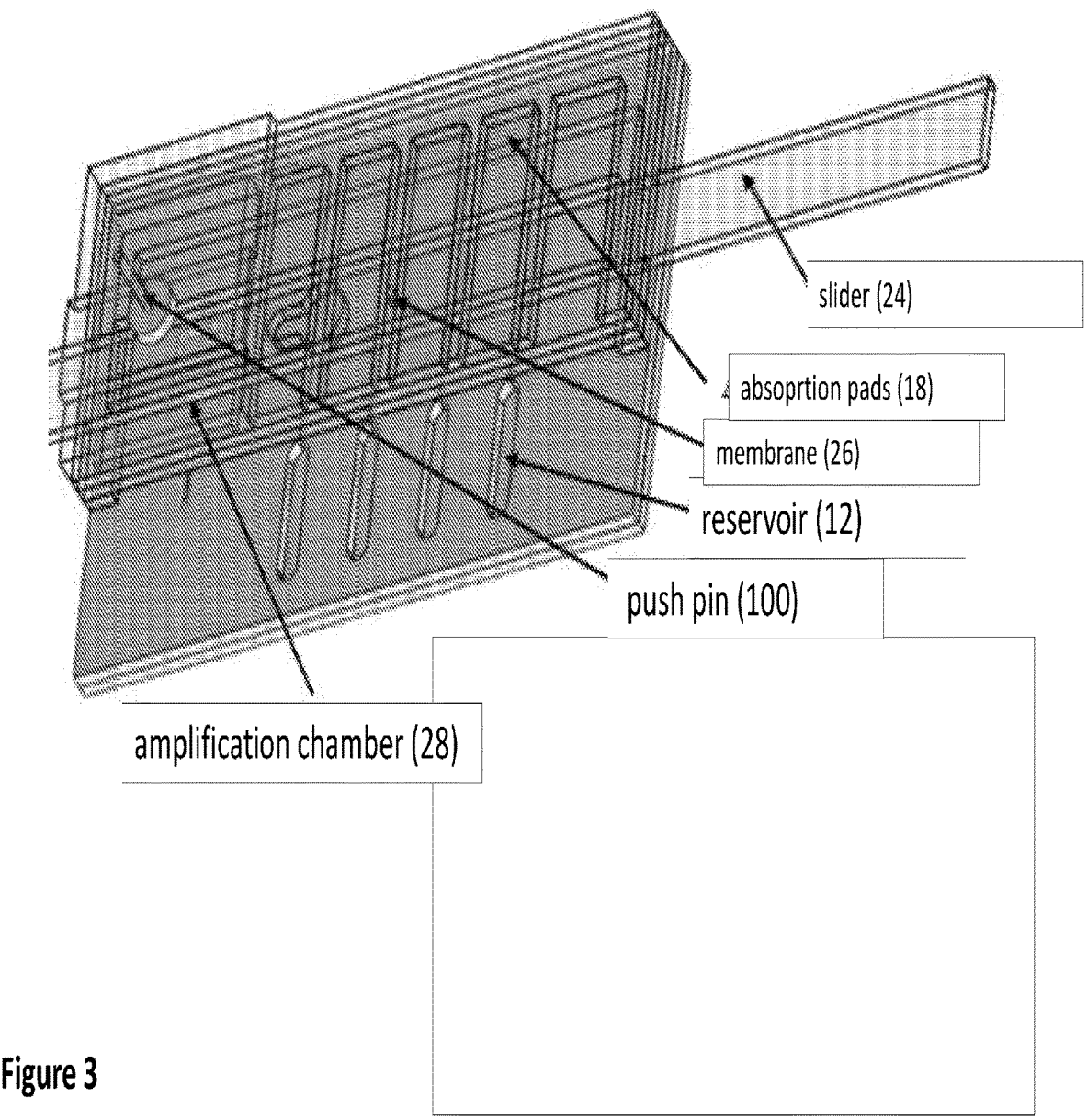
FIG. 3 shows a particular embodiment of the device in perspective view.

Here we describe a 'hybrid' approach where absorption pad wicking such as used in lateral flow strips and paper microfluidics is incorporated into a hard plastic chip with sample reservoirs and reaction chambers. This hybrid chip permits more complicated sample processing and is compatible with large (~100 µl) liquid volumes, liquid storage, and sealing against evaporation and aerosol contamination. FIG. 1 shows the basic components and features of the capillary-driven diagnostics device. A substrate (10) has a sample reservoir (12) and several liquid buffer/reagent reservoirs (14, 16). Opposing each reservoir is an adsorbing material (18, 20, 22) disposed in a chamber or opening formed in or on the substrate. A slidebar (24) supporting a porous material ('membrane') (26) can move in the directions indicated. The slidebar can be positioned such that the membrane provides a fluidic path or connection between a reservoir and opposing absorption material (called the absorption pad or receiving pad or chamber), The absorption materials can be different compositions (e.g., cellulose, silica glass fiber, etc. . . . ), porosities, and subjected to different treatments or coatings in order to optimize their wicking function (or amplification function) according to the properties (e.g., surface tension, density, viscosity) of the liquid in the opposing reservoir. The number of reservoirs, sample introduction reservoirs, or absorption pads can vary. For example, sample aliquots of a large sample volume or multiple samples could be added in steps. Also, several reservoirs can share a single absorption material. It is also understood that the direction of the slidebar translation could be reserved in some steps for more complicated protocols. The basic principle of capillary-drive fluid actuation to effect solid-phase extraction of NA from a sample is shown in FIG. 2, which depicts successive stages of operation. FIG. 3 shows a perspective of the chip as fabricated by laser machining of acrylic plastic parts and assembly. In FIG. 2a, the slider in which a porous NA-binding membrane is mounted can provide a flow path between a fluid reservoir and a receiving chamber packed with porous or fibrous material that serves as an absorption or receiving pad, and initially the slider is positioned such that there is no fluidic connection or flow pathway between the reservoirs and absorption pads. At this stage, the sample is introduced to the chamber (12) using a pipette, syringe, or other means. The sample may be pre-mixed with a lysing agent that lyses cells and viruses in the sample. Various lysing agents include salts, chaotropic agents, and enzymes such as proteinase K. These reagents serve to solubilize sample nucleic acids and also promote adsorption of nucleic acids to the membrane material mounted on the slidebar. Alternatively, the lysing agents can be dried in the introduction chamber, so that when liquid sample is introduced, the lysing agent(s) mix with the sample to effect lysis. In FIG. 2B, the slider is translated such that the membrane bridges the sample reservoir containing sample or sample lysate and a receiving pad, such that the liquid sample is wicked through the membrane onto the absorbent material. Specifically, the lysate is wicked through the NA-binding membrane and the nucleic acid contained in the lysate is now adsorbed on the membrane. Much of the lysate debris (proteins and other soluble components) is accumulated in the first wicking pad. FIG. 2C shows the next step, where the slider is moved so that the NA-binding membrane connects a second receiving pad with a second reservoir containing an ethanol-based wash solution, for example, such that the wash solution is wicked through the membrane, removing any residual proteins or compounds. Multiple washing steps can be effected by using multiple reservoir/receiving pad pairs. In the last step (2d or 2e), the nucleic acid captured on the membrane is used as a template for isothermal amplification with primers specific to the target analyte.

We developed two alternative designs (Option 1 and Option 2) for effecting this last step because hosting the amplification reaction on a porous material such as a wicking pad could encounter several problems. Normally, enzymatic amplification occurs in bulk solution. There is likely some inhibition of the amplification by the high-surface area of the absorbing material which will to some degree adsorb and immobilize enzyme, primers, and template. Second, the wicking pad material may exhibit significant autofluorence which will interfere with real-time monitoring of the fluorescence. Third, scaling of the reaction chamber to minimize evaporation may be necessary. Nevertheless, this first option (FIG. 2d), where the NA is eluted from the membrane and wicked into a receiving chamber, packed or partially packed with an absorption pad and to which amplification reagents and dye have been added in dry form, provides somewhat simpler chip and operation. As discussed below, these problems were avoided by selection of various adsorption pad materials.

In the second option (FIG. 2e), the slider has a push pin (FIG. 3, 100) that releases the NA-loaded membrane and inserts it into a chamber containing the amplification reagents, but no wicking material. In this option, the chamber is pre-filled with water. The dried reagents (polymerase, primers, nucleotides, buffer salts, and intercalating dye) are encapsulated with paraffin that melts upon heating (>60° C.), releasing and reconstituting the reagents. It is noted that the insertion of the cellulose membrane laden with captured DNA or RNA into a PCR reaction tube for subsequent thermal cycling is the standard protocol for FTA™ membranes. PCR and other amplification reactions can evidently tolerate FTA™ cellulose membranes, but the compatibility of other wicking pad materials (glass fiber, various polymers) needs to be evaluated. More specifically, we observe a specified volume of amplification reaction can tolerate certain pad or membrane materials for a specified liquid volume of amplification reaction. Also, the inhibition can be partly overcome by increasing the amount of polymerase and primer. Autofluorescence is due to excitation of the absorption pad material by the fluorescence light source can limit the detection sensitivity, a potential problem that is addressed below.

In both options, the chamber is heated to the incubation temperature (~65° C.) for real-time amplification. A CCD camera images the chamber for detection of a fluorescent signal. Thus, with three movements of the slider, the self-contained device eliminates the pipetting steps normally needed for sample transfer and additions of reagents for this type of molecular diagnostics protocol.

We tested various absorption materials for compatibility with enzymatic implication reactions, including isothermal LAMP. There were several absorption pad materials that proved compatible with LAMP reaction, Further, the use of luminescence detection successfully avoids problems with autofluorescence. In this case, reagents for luciferase-based bioluminecesce reactions as described by Gandelman et al. cited above. These reagents are included in the amplification reaction mixes, and their reactions occur simultaneously with amplification to produce a transient luminescence signal. Presence of the target analyte in the reaction is thus indicated by a bioluminescence signal which can be measured with a photodetection device, a CCD camera, or photographic film. The onset and intensity of the luminescence signal can be correlated with the amount of template amplified, thus allowing quantitative assays. In contrast to conventional fluorescence which requires an excitation light source that inadvertently creates background fluorescence from reaction components (rather than the amplicon product), porous wicking or absorption materials, or chip materials, the bioluminesence reaction produces a light signal without excitation light, and thus avoids background or autofluorescence that would otherwise limit detection of the true signal and assay sensitivity. Since many absorbing materials, such as cellulose, exhibit autofluorescence, the use of bioluminescence-based detection, instead of fluorescence, overcomes problems associated with fluorescence detection in chips and with amplification reactions in or near porous materials, and widens the choice and sizes of adsorption materials that can be utilized.

Materials and Methods

The chip is made as a bonded laminate of 1.6-mm thick sheets and 250-micron thick films of PMMA (polymethylmethacrate, "acrylic", McMaster-Carr, Elmhurst, IL), Microseal™ "PCR" tape (Biorad, Hercules, Calif., MSB-1001), and 3M™ (St. Paul, MN) 9500PC double-sided tape. The parts are designed by computer-aided design (CAD) software (SolidWorks™ or AutoCAD™) and 2-dimensional DXF 'drawing' files program the cutting paths made by laser machining using a 30-watt CO2 laser engraving system (Universal Laser Systems Model, Scottsdale, AZ, VLS 3.50). The smallest feature size is 0.5 mm, and the part tolerances are ±0.05 mm. Perspective drawings and a photograph of the device are shown in FIG. 2. The body of the device measures xx mm (L)×yy mm (W)×zz mm (H). The slidebar dimensions are xx mm (L)×yy mm (W)×zz mm (H). Each reservoir holds 70 µl of liquid. The NA-binding membranes are cut from Whatman FTA™ ("Classic") cellulose cards in a rectangular shape measuring approximately. The membrane are mounted snuggly in a slot cut in the slidebar. The absorption pads are patterned from 1-mm thick Whatman GB004 gel blot paper (pure cellulose). The reagents include QIAGEN DNEasy™ AL Lysis/Binding buffer (~6M guanidium HCL), Whatman FTA™ purification buffer or a 50%-50% ethanol:water for wash solution, and TE buffer (pH 7.2) for elution.

The target is from cultures of *Salmonella enterica* cells, a gram negative bacillus and causative agent of food poisoning.

In addition to primers and template, LAMP reaction mixtures (15 µL) contained 9 µL OptiGene Isothermal Master Mix. ISO-100 (Optigene, UK) and 0.5 µL EvaGreen dye (Biotium, Hayward, CA). Amplification was monitored using the BioRad Real Time PCR system with the following settings: 60 cycle of 1 min at 63° C. Fluorescence data were collected at 1-min intervals.

The six LAMP primers used (and final concentrations) were:

```
F3:
5'-GATCTGAATCCGACCAACCG-3' (0.2 µM);

B3:
5'-AACGCCCACGCTCTCGCA-3' (0.2 µM);

Loop F:
5'-AACGCCCACGCTCTCGCA-3' (0.8 µM);

Loop B:
5'-AACGCCCACGCTCTCGCA-3' (0.8 µM);

FIP:
5'-AAATCCGTCCAGTGGTFTTTTTTTGAAAATCGTT
GTATCTCCG-3' (1.6 µM);

BIP:
5'-CCGAAACCACTGGACGGATTTTTATTTTTAATCT
AAAACAAACATC-3' (1.6 µM)
```

For LAMP amplification, we used an isothermal mastermix (Optigene. Ltd., UK) with *Salmonella* primer. For incubation at 65° C., the chip is placed on a hotplate which is adjusted to control the temperature of the amplification chamber as determined by a thermocouple inserted in the amplification chamber for calibration.

The CCD camera images were analyzed with MATLAB™ software image processing utilities. Image pixel intensities were converted to fluorescence intensity to generate curves of relative fluorescence as a function of amplification times. Parallel benchtop procedures for comparison and to assess the utility of the membrane for capturing nucleic acid from Detail of Membrane Shape and Mounting on Slidebar In each stage, the membrane connects the supply reservoir of liquid to the wicking pad.

Results

Figure 4:
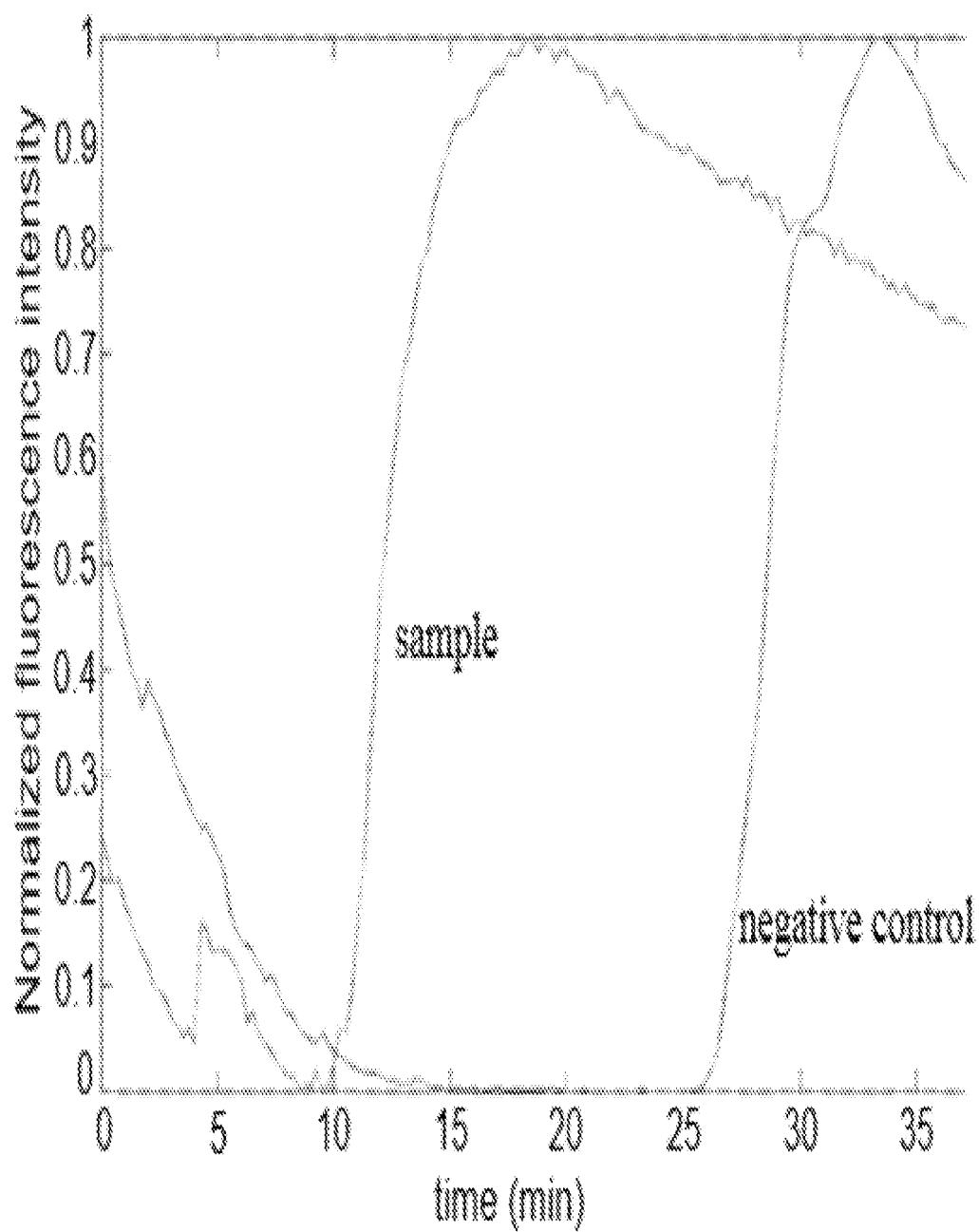
FIG. 4 is the relative fluorescence signal as a function of time in operating the device with a sample containing a specific nucleic acid.

Initially, we tested the chips with colored dyes in water, ethanol-water solutions, lysis butler (6M guanidinium HCl), aqueous solutions with various detergents (Tween™, SDS, sodium dodecylsulfate), and liquid wax to visualize flow for different types of liquids. We explored numerous fibrous and porous materials as wicking pads, including silica glass fiber mats, various grades of Porex™ (sintered polyethylene particles), nitrocellulose, pure cellulose. All adsorption materials proved workable, including those with silica glass fiber and cellulose membranes, which produced high fluorescence signals during amplification. FIG. 4 shows the fluorescence intensity, as measured with a CCD camera, as a function of amplification time for the chip described above, using the OPTION 2 where the membrane laden with isolated nucleic acid is inserted into a liquid reaction mix. The sample shows an increase in fluorescence at about 12 minutes, while the negate control needs more than 25 minutes. This is typical behavior for LAMP reactions, positive samples show earlier development of fluoresnce, than negative samples which shows delayed fluorescence due to non-specific amplification (e.g., primer-dimers). A criteria for distinguishing between positives and negatives based on the threshold time to fluorescence is done by optimization specific to sample type and range of target analyte. Moreover, further optimization of reagents and primers can delay or suppress negative control signals. Our purpose is to show the feasibility of the device for isolating nucleic acids from samples, amplification, and detection in the capillary-action slider chip. The design particulars described above represent working examples of test devices, but there is considerable latitude in changing dimensions, shapes, and materials to implement the inventive approaches described here with regard to effecting fluid actuation by capillary forces and controlling flow paths with a sliding mechanism, and its application to a diagnostics test device.

Figure 5:
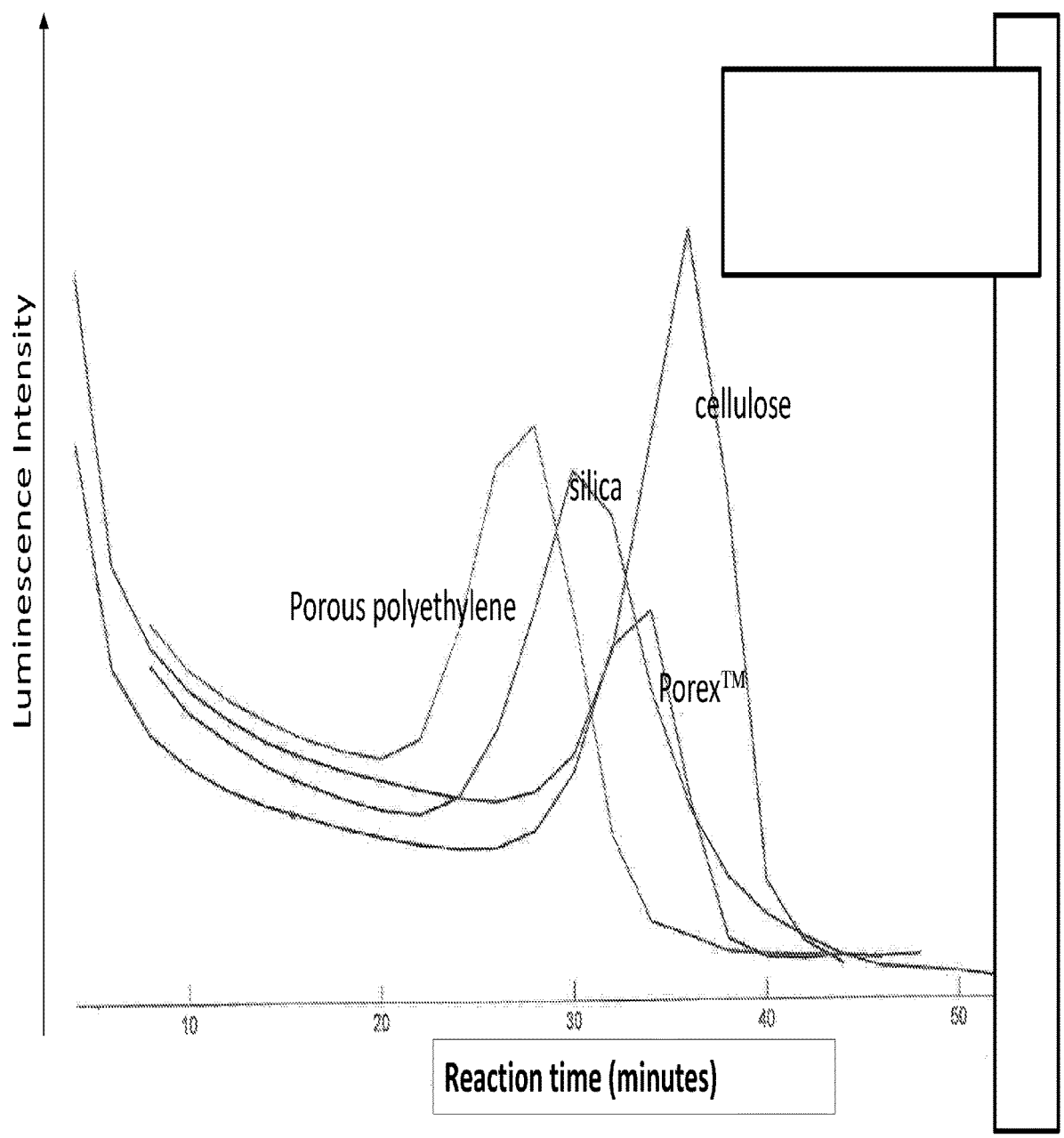
FIG. 5 shows luminescent curves for enzymatic amplification on various porous absorbing pad materials used the chip.

The feasibility of NA amplification on the absorption pad (Option 1 in FIG. 2) was explored using various porous materials to ascertain compatibility with amplification reactions. We used a bioluminescent reporter assay ('BART', Lumora, Ltd., Cambridge, UK) coupled to the enzymatic amplification to avoid autofluorescence issues. An acrylic chip with a 25-μl microfluidic chamber is packed to varying fill fractions with porous material. The amplification reaction mixture is injected into the chamber, the chamber inlet and outlet ports are sealed with PCR-compatible tape, the chip placed on a heated stage, and the fluorescence of the chamber is monitored with a CCD camera. We successfully utilized adsorption materials comprised of one of 1) cellulose, 2) silica glass fibers, 3) nitrocellulose, and sintered polyethylene (Porex™). The luminescence signals for various adsorption materials is shown in FIG. 5. Reactions using reagents dried on the adsorbing material also produced similar luminescence characteristics.

Discussion

Our main objective in this concept validation and feasibility study was to demonstrate that a moderately complex diagnostic protocol (NA extraction and isolation combined with enzymatic amplification and real-time fluorescence detection) could be implemented in a simple scheme required no external pumping or valves. While wicking forces serve the basis of lateral flow strip immunoassays, the extension of 'paper' microfluidics and capillary flow techniques to molecular diagnostics has Molecular diagnostics has more complicated operations, larger volumes of sample and reagents, more stringent requirements with regard to temperature control, purity, and optical transmission.

While more optimization is feasible, the results to date demonstrate the feasibility of using passive wicking action and simple sliding actuation for both fluid actuation and flow control to effect a relatively complex diagnostics protocol.

Supplemental Information

We explored a number of materials for wicking pads including various polymers, silica glass fiber mats, Porex™, and cellulose. Our selection of absorption pads was based primarily on wicking power to draw liquid from the reservoir through the NA-binding membrane mounted on the slidebar.

The manual actuated slidebar could also be motorized for more automated control.

Several videos of chip operation are available.

Capillary-Action Microfluidic Chip for POC Diagnostics

Microfluidics technology encompasses methods of fabrication and applications of miniaturized devices and systems for fluid-based processing and analysis. An important application area is medical diagnostics where clinical specimens such as blood, urine, oral fluids are analyzed for biomarkers (nucleic acids, proteins, or other biomolecules) that are indicators of health or disease. Diagnostics tests are typically performed in centralized laboratories equipped with sophisticated and expensive instrumentation, and staffed by trained technicians and specialists. A trend in healthcare is the emergence of point-of-care diagnostics where low-cost portable devices are used to perform medical tests outside of the laboratory. These devices can provide rapid (<1 hour) test results, and can be operated by non specialists with minimal training. As such, they can be used in doctors and dentists offices, school infirmaries, rural clinics, pharmacies, and even at home. Related uses include food and water testing, detection of bioterrorism agents, and environmental monitoring.

One useful dichotomy separates microfluidic devices into one of two types. The first type is comprised of substrates ('chips') made in hard or soft plastics, glass, silicon, ceramics, or other materials. The substrate hosts a network of channels, conduits, chambers, manifolds, embedded filters, sieves, mixing elements where the sample and reagents are processed and analyzed. Beyond the simplest operations, such systems require means of fluid actuation and flow control. Fluid actuation and flow control in principle could be implemented by fabricating pumps and valves directly on the chip, but integration of such components into chips proves to be technically challenging and expensive. Another avenue is for the chip to mate with an instrument that provides external pumping (e.g., with programmable syringe pumps), and some mechanical means for gating flow on the chip, such as by diaphragm valves and external solenoids. A companion instrument could also provide external heating or cooling for the chip, and detection of fluorescence or other optical effects. Such companion instrumentation adds cost to the point of care diagnostics. It can also create 'bottlenecks' in testing if many sample chips need to be tested, Further, in the case of fluid actuation it typically requires that multiple fluid connections need to be made between the chip and the instrument which complicates it use and compromises reliability. Thus, there is a desire for more autonomous and less-instrumented or non-instrumented chips.

A second type of microfluidic device relies on capillary flow through porous media. Fluid actuation is provided by the wicking action of absorbent pads. The lateral flow strip, such as the common home pregnancy test, is a commercially successful example of such a device. In the last several years, there has been considerable interest in so-called paper microfluidics where flow paths are defined in filter paper by for example printing impervious polymers or waxes to delineate channels and interconnections. In general, such paper microfluidics is comparatively limited in functionality with respect to sample and liquid volumes, flow control, temperature control, and reagent storage.

The disclosure here is in one respect a hybrid device that combines the functionality of plastic substrate devices, with the fluid actuation by capillary action afforded by wicking pads. The disclosure describes a molecular diagnostics protocol that includes lysis, nucleic acid isolation by solid-phase extraction, enzymatic amplification, and fluorescence detection of the amplification product. Moreover, the solid-phase extraction comprises separate steps of loading a lysate on a nucleic-acid binding membrane, washing the membrane to remove proteins and other inhibitors, and bringing the membrane in contact with an amplification reaction mix for specific amplification of gene sequences immobilized on the membrane. This is a considerably more ambitious combination of processing steps than can be typically implemented with other paper microfluidic architectures. Further, all of these processing steps are effected with a simple intermittent translational motion of a slider, and avoids the need for pipetting, sample transfer, addition of reagents or buffers, or use of complicated supporting instrumentation such as centrifuges or syringe pumps.

Many microfluidic diagnostics devices have been reported for immunoassays, and for nucleic acid amplification testing (enzymatic amplification, e.g., PCR, and fluorescence detection of the amplification product). Comparatively less work has addressed the processing steps from raw sample (blood, oral fluid, food samples) to isolated nucleic acids suitable for enzymatic amplification. The device disclosed here can accommodate relatively large volume (>100 microliters), heterogeneous samples.

The device described here integrates steps for sample preparation, including (optionally) plasma extraction, lysis, and nucleic acid isolation (extraction and purification of soluble DNA and RNA in the lysate), with amplification and detection.

The shape and position of the nucleic acid capture membrane mounted on the slidebar enables efficient and reliable transfer of liquid from the reservoir, through the NA capture membrane, and adsorption on the wicking pad. In one embodiment, we use an inverted U-shape for the somewhat deformable, flexible NA binding membrane, where one end of the membrane protrudes into the liquid reservoir when the slidebar is so positioned, and the other end make intimate contact with the absorption pad. This allows the porous membrane to form a fluidic "bridge" between the reservoir filled with liquid and the dry absorption pad. A recess can be made in the slidebar to seat the membrane, so that the slidebar movement is not impaired by the membrane.

One consideration of molecular diagnostics devices is material compatibility with the chemical and biochemical reactions performed on the chip, and the optical detection of a signal. In the first case, some materials, many adhesives and tapes, and solvents used for bonding interfere or inhibit the reactions. In particular, even residual amounts of some substances denature or otherwise deactivate enzymes used in the assay. We have demonstrated functional devices using the following materials for the substrate that include: acrylic, polycarbonate, cyclic olefin copolymer. Using the following means of bonding substrate materials that include: thermal-pressure bonding, solvent bonding with acetonitrile, ultrasonic welding, PCR-compatible adhesive tapes (PCR Sealers) made by Biorad, Inc, and several types of adhesive tapes from 3M (e.g., 9490 LE, 9500 PC). Materials for the wicking pad include cellulose, nitrocellulose, various silica glass fiber mats, Porex™, and other spongey, adsorbent materials, and especially paper-based products. These can be treated with hydrophilic coatings such as detergents (Tween, SDS) to improve or modify wicking action. Materials for the nucleic acid capture membrane include silica glass fibers, cellulose, Whatman FTA™ filter paper, alumina, or ceramic materials).

In one embodiment, we used a luminescent nucleic acid isothermal amplification assay similar to LAMP (loop-mediated amplification) from Eiken Chemical, and similar NA amplification reaction technologies from Twist DX and Lucigen (Madison, Wisconsin). These assays utilized a DNA-intercalating dye (SYBR Green, SYTO Green, or EVAGreen™) to produce a fluorescence signal of the amplification product. In still another embodiment, we coupled the amplification reaction with a luciferase bioluminesence reporter reaction (Lumora Inc., Cambridge UK) to generate a luminescent signal. This later approach eliminates the need for a separate ultraviolet or blue light source to excite fluorescence, and eliminates autofluorescence from plastics or membrane materials interfering with the amplified product siginal.

We can detect the amplified DNA while it is still captured on the membrane, or if it has desorbed into the bulk solution of the amplification reaction. Either, produces a measureable increase in fluorescence, but for membrane-immobilized DNA, the bioluminescence assay is advantageous to reduce the background fluorescence of the membrane material.

It is noted that particular enzymes used in the assay work for both RNA and DNA targets, and some polymerases can be supplemented with reverse transcriptase enzymes to convert RNAs to cDNAs before DNA amplification.

Spray coatings, such as hydrophobic coatings that create a "superhydrophic" surface (e.g., Rustoleum Never-Wet™) are useful for coating parts of the slidebar to reduce leakage and prevent wetting of the slider. Sealants such as pasty or viscous petroleum or silicone gels, or similar, can be used reduce leakage of fluids due to slidebar movement.

The slider action can be motorized for more automated operation. Nubs or notches can be formed in the slidebar to indicate and facilitate its correct positions during the operation of the device.

Longterm storage of the reagents can be facilitated by storing the liquids in the reservoirs that have additionally a frangible seal at the orifice connecting the reservoir with the membrane, and that can be ruptured at the time use.

All reagents and enzymes can be pre-stored in the chip in lyophilized (free dried) form.

The fluorescence can be detected with a cellphone camera, a USB microscope, a photodetector, or other low-cost optical detector or camera. The excitation signal for fluorescence can be provided by a light-emitting diode of specified emission wavelength.

Parallel sets of reservoirs, channels and slidebars can be assembled in one device for multiplex (multiple analyte) analysis.

While the invention has been described with reference to the embodiments above, a person of ordinary skill in the art would understand that various changes or modifications may be made thereto without departing from the scope of the claims.

The invention claimed is:

1. A testing method that integrates a processing and an analysis of a sample containing an analyte, comprising:
   (a) loading the analyte onto a binding membrane of a testing device comprising:
      a substrate having an upper area surface that defines at least three laterally aligned reagent reservoirs and a lower area surface upon which are disposed at least three sections of adsorbing material, wherein each of the sections is aligned with at least one of the at least three reservoirs; and
      a slidebar upon which is mounted the binding membrane and which slidebar is slidably attached to the substrate so that the sidebar can be slidably moved along a hypothetical horizontal plane that bisects the substrate upon application of a horizontal-directed force;
      wherein the slidebar may be slid in the horizontal plane to bridge, in series, one of the at least three reservoirs and one of the at least three sections of absorbing material to place the reservoir and the section of adsorbing material bridged in fluidic communication with one another,
   (b) placing a reagent to isolate, purify or concentrate the analyte into each of the at least three laterally aligned reagent reservoirs independently;
   (c) processing the sample to derive the analyte by sliding the slidebar in the hypothetical horizontal plane to bridge in series each of the at least three laterally aligned reagent reservoirs wherein the movement of the slidebar causes the sample or reagent liquids to be wicked via capillary force through the membrane so that the analyte is isolated, purified and/or concentrated to a captured analyte; and
   (d) eluting the captured analyte from the membrane.

2. The method of claim 1 wherein the binding membrane of the device is selected from a porous material and a fibrous material that can bind nucleic acids.

3. The method of claim 1 wherein at least one of the sections of adsorbing material of the device is disposed in a chamber or opening that is defined by the lower area surface of the substrate.

4. The method of claim 1 wherein the adsorbing material of the device is independently selected from silica glass, fiber, or cellulose.

5. The method of claim 1 wherein the binding membrane of the device comprises a wick adapted to facilitate fluidic communication with a liquid in a reservoir.

6. The method of claim 1 wherein a slidable movement of the slidebar of the device along the plane is actuated by a motor.

7. The method of claim 1 wherein a slidable movement of the slidebar is controlled by stops or notches that create resistance at movement when the slidebar is correctly positioned.

8. The method of claim 1 wherein a slidable movement of the slidebar of the device is halted by the stops or notches but can be continued by increasing a force on the slidebar.

9. The method of claim 1 wherein step (b) is performed before step (a) and the reservoirs are each sealed by a frangible seal and the method further includes breaking the frangible seal to access each of the reagents prior to the performance of step (c).

10. The method of claim 1 wherein the reagents are each independently selected from a reagent that isolates the analyte, a regent that purifies the analyte, and a reagent that concentrates the analyte.

11. The method of claim 1 wherein each of the reagents is independently selected from a lysing reagent, a wash buffer, and a binding reagent.

12. The method of claim 1 wherein the analyte is selected from whole blood, blood plasma, blood serum, urine, saliva, stool, food, and water.

13. The method of claim 1 wherein the binding membrane is a nucleic acid binding substrate.

14. The method of claim 1 wherein the captured analyte is a nucleic acid, and it is eluted by exposing the binding membrane into an enzymatic reaction mixture that comprises a primer specific to the nucleic acid.

15. The method of claim 14 wherein the enzymatic reaction mixture further comprises a reporter selected from a dye that is optically detectable, a fluorescent reporter, and an optical absorption reporter.

16. The method of claim 14 wherein the enzymatic reaction mixture is disposed within a chamber on the device or is contained within an absorption pad.

17. A method comprising:
  a. loading a target nucleic acid-containing lysate onto a nucleic acid-binding membrane of a testing device comprising:
    i. a substrate having an upper area surface that defines at least three laterally aligned reagent reservoirs and a lower area surface upon which is disposed at least three sections of adsorbing material, wherein each of the sections is aligned with at least one of the at least three reservoirs; and
    ii. a slidebar upon which is mounted the binding membrane, wherein the slidebar is slidably attached to the substrate so that it can be slidably moved along a hypothetical horizontal plane that bisects the substrate upon application of a horizontal-directed force;
    wherein the slidebar may be slid in the horizontal plane to bridge, in series, one of the at least three reservoirs and one of the at least three sections of absorbing material to place the reservoir and the section of adsorbing material bridged in fluidic communication with one another,
  b. placing into the at least three laterally aligned reagent reservoirs a washing buffer that removes proteins and other inhibitors, and an amplification reaction reagent that is specifically designed to amplify a nucleic acid sequence of the nucleic acid;
  c. processing the target nucleic acid-containing lysate to isolate the target nucleic acid by sliding the slidebar in the hypothetical horizontal plane to bridge in series each of the at least three laterally aligned reagent reservoirs wherein the movement of the slidebar causes the lysate or reagent liquids to be wicked via capillary force through the membrane so that the target nucleic acid is isolated, purified and/or concentrated; and
  d. eluting the target nucleic acid from the membrane.

18. The method of claim 17 wherein the target nucleic acid-containing lysate is prepared from a material selected from plasma, blood serum, urine, saliva, stool, food, and water.

* * * * *